(12) United States Patent
Caroff et al.

(10) Patent No.: US 8,466,156 B2
(45) Date of Patent: Jun. 18, 2013

(54) 2-PHENYL-4-CYCLOPROPYL-PYRIMIDINE DERIVATIVES

(75) Inventors: Eva Caroff, Ranspach-le-Haut (FR); Emmanuel Meyer, Aarau (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 201 days.

(21) Appl. No.: 12/936,664

(22) PCT Filed: Apr. 9, 2009

(86) PCT No.: PCT/IB2009/051498
§ 371 (c)(1),
(2), (4) Date: Oct. 6, 2010

(87) PCT Pub. No.: WO2009/125365
PCT Pub. Date: Oct. 15, 2009

(65) Prior Publication Data
US 2011/0028484 A1    Feb. 3, 2011

(30) Foreign Application Priority Data

Apr. 11, 2008    (WO) .................. PCT/IB2008/051389

(51) Int. Cl.
*C07D 403/12*    (2006.01)
*A61K 31/506*    (2006.01)

(52) U.S. Cl.
USPC ............ 514/252.14; 514/252.18; 514/252.19; 514/252.2; 544/295

(58) Field of Classification Search
USPC ........... 544/295; 514/252.14, 252.18, 252.19, 514/252.2
See application file for complete search history.

(56) References Cited

U.S. PATENT DOCUMENTS

| | | | |
|---|---|---|---|
| 6,855,715 | B1 | 2/2005 | Liebeschuetz et al. |
| 8,058,263 | B2 | 11/2011 | Caroff et al. |
| 8,067,419 | B2 | 11/2011 | Binkert et al. |
| 2003/0060474 | A1 | 3/2003 | Bryant et al. |
| 2005/0038037 | A1 | 2/2005 | Bryant et al. |
| 2005/0065163 | A1 | 3/2005 | Bryant et al. |
| 2008/0194576 | A1 | 8/2008 | Caroff et al. |
| 2008/0234272 | A1 | 9/2008 | Binkert et al. |
| 2010/0261678 | A1 | 10/2010 | Caroff et al. |
| 2011/0046089 | A1 | 2/2011 | Caroff et al. |
| 2012/0053149 | A1 | 3/2012 | Caroff et al. |

FOREIGN PATENT DOCUMENTS

| | | |
|---|---|---|
| EP | 0 407 200 A1 | 1/1991 |
| JP | 5303586 | 6/1978 |
| WO | WO 02/098856 | 12/2002 |
| WO | WO 2004/052366 | 6/2004 |
| WO | WO 2004/092189 A1 | 10/2004 |
| WO | WO 2006/114774 | 11/2006 |
| WO | WO 2008/044217 | 4/2008 |
| WO | WO 2008/050301 | 5/2008 |
| WO | WO 2008/128647 | 10/2008 |
| WO | WO 2009/069100 | 6/2009 |
| WO | WO 2009/080226 | 7/2009 |
| WO | WO 2009/080227 | 7/2009 |
| WO | WO 2009/125366 | 10/2009 |
| WO | WO 2010/116328 | 10/2010 |
| WO | WO 2010/122504 | 10/2010 |

OTHER PUBLICATIONS

Feokistov et al., Adenosine A2B receptors, Pharmacological Reviews, vol. 49, No. 4, pp. 381-402, 1997.*
Bélanger, G., et al., "New Approach to Aphidicolin and Total Asymmetric Synthesis of Unnatural (11R)-(-)-8-Epi-11-hydroxyaphidicolin by Tandem Transannular Diels—Alder/Aldol Reactions", J. Org. Chem., vol. 65, pp. 7070-7074, (2000).
Charette, A., et al., "Enantioselective Cyclopropanation of Allylic Alcohols with Dioxaborolane Ligands: Scope and Synthetic Applications", J. Am. Chem. Soc., vol. 120, pp. 11943-11952, (1998).
Gould, P.L., "Salt Selection for Basic Drugs", International Journal of Pharmaceutics, vol. 33, pp. 201-217, (1986).
Parlow, J.J., et al., "Piperazinyl-glutamate-pyridines as Potent Orally Bioavailble P2Y12 Antagonists for Inhibition of Platelet Aggregation", Bioorganic & Medicinal Chemistry Letters, vol. 19, pp. 4657-4663, (2009).
Parlow, J.J., et al., "Piperazinyl-glutamate-pyrimidines as Potent P2Y12 Antagonists for Inhibition of Platelet Aggregation", Bioorganic & Medicinal Chemistry Letters, vol. 19, pp. 6148-6156, (2009).
Remington, "The Science and Practice of Pharmacy, 21$^{st}$ Edition (2005), Part 5, Pharmaceutical Manufacturing" [published by Lippincott Williams & Wilkins].
Sheppard, G., et al., "Discovery and Optimization of Anthranilic Acid Sulfonamides as Inhibitors of Methionine Aminopeptidase-2: A Structural Basis for the Reduction of Albumin Binding", J. Med. Chem., vol. 49, pp. 3832-3849, (2006).
Parlow, J.J. et al., "Piperazinyl glutamate pyridines as potent orally bioavailable $P2Y_{12}$ antagonists for inhibition of platelet aggregation," J. Med. Chem., 2010, 53, 2010-2037.
Alpegiani et al., "On the Preparation of 4-Hydroxymethyl-5-1,3-Dioxol-2-One," Synthetic Communications, 1992, vol. 22, No. 9, pp. 1277-1282.
Amir et al., "Treatment of Thrombotic Thrombocytopenic Purpura with Antiplatelet Drugs," Blood, 1973, vol. 42, No. 1, pp. 27-33.
Antithrombotic Trialists' Collaboration, "Collaborative Meta-Analysis of Randomised Trials of Antiplatelet Therapy for Prevention of Death, Myocardial Infarction, and Stroke in High Risk Patients," British Medical Journal, 2002, vol. 324, pp. 71-86.
Balduini et al., "Platelet Aggregation in Platelet-Rich Plasma and Whole Blood in 120 Patients with Myeloproliferative Disorders," American Journal of Clinical Pathology, 1991, vol. 95, No. 1, pp. 82-86.

(Continued)

*Primary Examiner* — Deepak Rao
(74) *Attorney, Agent, or Firm* — Hoxie & Associates LLC

(57) ABSTRACT

The present invention relates to 2-phenyl-4-cyclopropyl-pyrimidine derivatives and their use as $P2Y_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

10 Claims, No Drawings

OTHER PUBLICATIONS

Bartoli et al., "Reaction of Dianions of Acyclic Beta-Enamino Ketones with Electrophiles. 3. Nitriles: Synthesis of Pyridine and Pyrimidine Derivatives," Journal of Organic Chemistry, 1992, vol. 57, No. 22, pp. 6020-6025.

Bertrand et al., "Randomized Multicenter Comparison of Conventional Anticoagulation Versus Antiplatelet Therapy in Unplanned and Elective Coronary Stenting: The Full Anticoagulation Versus Aspirin and Ticlopidine (FANTASTIC) Study," Circulation, 1998, vol. 98, pp. 1597-1603.

Born et al., "The Aggregation of Blood Platelets," The Journal of Physiology, 1963, vol. 168, pp. 178-195.

Brighton et al., "Antiphospholipid Antibodies and Thrombosis," Bailliere's Clinical Haematology, 1994, vol. 7, No. 3, pp. 541-557.

Caprie Steering Committee, "A Randomised, Blinded, Trial of Clopidogrel Versus Aspirin in Patients at Risk of Ischaemic Events (CAPRIE)," The Lancet, 1996, vol. 348, pp. 1329-1339.

Collins et al., "Review Article: Platelets in Inflammatory Bowel Diease—Pathogenic Role and Therapeutic Implications," Alimentary Pharmacology and Therapeutics, 1997, vol. 11, pp. 237-247.

Database Chemcats, Chemical Abstracts Service, Columbus, OH, USA; XP002420714; Order No. (ON) CGX-3221820.

Database Chemcats, Chemical Abstracts Service, Columbus, OH, USA; XP002420715; Order No. (ON): T5569369, T5467386.

Davies et al., "Intramyocardial Platelet Aggregation in Patients with Unstable Angina Suffering Sudden Ischemic Cardiac Death," Pathophysiology and Natural History—Platelets, Circulation, 1986, vol. 73, No. 3, pp. 418-427.

Felfernig-Boehm et al., "Early Detection of Preeclampsia by Determination of Platelet Aggregability," Thrombosis Research, 2000, vol. 98, pp. 139-146.

Fox et al., "Benefits and Risks of the Combination of Clopidogrel and Aspirin in Patients Undergoing Surgical Revascularization for Non-ST-Elevation Acute Coronary Syndrome: The Clopidogrel in Unstable Angina to Prevent Recurrent Ischemic Events (CURE) Trial," Circulation, 2004, vol. 110, pp. 1202-1208.

Frstner et al., "Iron-Catalyzed Cross-Coupling Reactions," Journal of the American Chemical Society, 2002, vol. 124, No. 46, pp. 13856-13863.

Halushka et al., "Protective Effects of Aspirin in Endotoxic Shock," The Journal of Pharmacology and Experimental Therapeutics, 1981, vol. 218, No. 2, pp. 464-469.

Hovens et al., "Aspirin in the Prevention and Treatment of Venous Thromboembolism," Journal of Thrombosis and Haemostasis, 2006, vol. 4, pp. 1470-1475.

Iyer et al., "Synthesis of Iodoalkylacylates and Their Use in the Preparation of S-Alkyl Phosphorothiolates," Synthetic Communications, 1995, vol. 25, No. 18, pp. 2739-2749.

Kharbanda et al., "Prevention of Inflammation-Induced Endothelial Dysfunction: A Novel Vasculo-Protective Action of Aspirin," Circulation, 2002, vol. 105, pp. 2600-2604.

Megalopoulos et al., "Recurrent Arterial Thromboses in a Woman with Heparin Induced Thrombocytopenia, Successfully Managed with Iloprost Followed by Clopidogrel. An Alternative Therapeutic Option for Heparin Induced Thrombocytopenia Type II Syndrome," International Angiology, 2006, vol. 25, No. 1, pp. 84-89.

Mehta et al., "Effects of Pretreatment with Clopidogrel and Aspirin Followed by Long-Term Therapy in Patients Undergoing Percutaneous Coronary Intervention: The PCI-CURE Study," The Lancet, 2001, vol. 358, pp. 527-533.

Nogard, "Cangrelor: A Novel P2Y12 Receptor Antagonist," Expert Opinion on Investigational Drugs, 2009, vol. 18, No. 8, pp. 1219-1230.

Notice of Allowance issued Jun. 27, 2011, in U.S. Appl. No. 12/936,661, 9 pages.

Office Action issued Jun. 21, 2012, in U.S. Appl. No. 12/745,358, 8 pages.

Office Action issued Jan. 19, 2011, in U.S. Patent Application No. 12/445,352, 23 pages.

Office Action issued Jan. 21, 2011, in U.S. Patent Application No. 12/936,661, 7 pages.

Office Action issued Oct. 1, 2012, in U.S. Appl. No. 12/745,358, 7 pages.

Office Action issued Oct. 28, 2010, in U.S. Appl. No. 11/912,545, 14 pages.

Payne et al., "Beneficial Effects of Clopidogrel Combined with Aspirin in Reducing Cerebral Emboli in Patients Undergoing Carotid Endarterectomy," Circulation, 2004, vol. 109, pp. 1476-1481.

Shao et al., "Phenoxyphenyl Pyridines as Novel State-Dependent, High-Potency Sodium Channel Inhibitors," Journal of Medicinal Chemistry, 2004, vol. 47, No. 17, pp. 4277-4285.

Stathakis et al., "Platelet Dysfunction in Essential Thrombocythaemia," Annals of Clinical Research, 1974, vol. 6, pp. 198-202.

Sun et al., "A General Synthesis of Dioxolenone Prodrug Moieties," Tetrahedron Letters, 2002, vol. 43, pp. 1161-1164.

Thorsen et al., "The Treatment of the Hemolytic-Uremic Syndrome with Inhibitors, of Platelet Function," The American Journal of Medicine, 1979, vol. 66, pp. 711-716.

Triadou et al., "Platelet Function in Sickle Cell Disease During Steady State," Nouvelle Revue Francaise Hematologie, 1990, vol. 32, pp. 137-142.

University of Perugia, "Aspirin for the Prevention of Recurrent Venous Thromboembolism and Cardiovascular Events," Sep. 13, 2005, http://www.clinicaltrials.gov/ct/show/NCT00222677, 3 pages.

Yao et al., "Clopidogrel is More Effective Than Aspirin as Adjuvant Treatment to Prevent Reocclusion After Thrombolysis," American Journal of Physiology, 1994, vol. 267, pp. H488-H493.

* cited by examiner

2-PHENYL-4-CYCLOPROPYL-PYRIMIDINE DERIVATIVES

CROSS REFERENCE TO RELATED APPLICATIONS

This application is a United States Application under 35 U.S.C. 371 claiming benefit of PCT Application No. PCT/IB32009/051499, filed on Apr. 9, 2009, which claims the benefit of PCT Application No. PCT/IB2008/051385, filed on Apr. 11, 2008, the contents of each of which are incorporated herein by reference.

FIELD OF THE INVENTION

The present invention relates to certain 2-phenyl-4-cyclopropyl-pyrimidine derivatives and their use as $P2Y_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

BACKGROUND OF THE INVENTION

Haemostasis is referred to as the natural balance of maintaining the fluidity of the blood in the vascular system and preventing excessive blood loss subsequent to blood vessel injury by rapid formation of a solid blood clot. After vascular damage, contraction of the vessels and platelet adhesion occur immediately followed by aggregation of the platelets, activation of the coagulation cascade and finally also of the fibrinolytic system. Haemostatic abnormalities can lead to excessive bleeding or thrombosis, both life-threatening situations.

A series of antiplatelet agents have been developed over the past several years based on different mechanisms of action. The most widely used agent in antiplatelet therapy is aspirin, which irreversibly inhibits cyclooxygenase-1 and thereby affecting the thromboxane pathway. Although not optimally efficacious, treatment with aspirin remains the standard therapy against which new therapeutics are compared and judged.

Other drugs like the phosphodiesterase inhibitors dipyridamole and cilostazol, as well as the vitamin K antagonists (warfarin), are marketed but do not show all desirable features for such drugs. Three intravenously applicable, potent GPIIb/IIIa receptor antagonists (abciximab, eptifibatide, and tirofiban) blocking platelet aggregation are available on the market. Besides, some orally active GPIIb/IIIa antagonists (e.g. sibrafiban, xemilofiban or orbofiban) have not been successful in clinical development so far.

Adenosine 5'-diphosphate (ADP) is a key mediator in platelet activation and aggregation interfering with two platelet ADP receptors $P2Y_1$ and $P2Y_{12}$.

Antagonists of the platelet ADP receptor have been identified and display inhibition of platelet aggregation and antithrombotic activity. The most effective antagonists known so far are the thienopyridines ticlopidine, clopidogrel and CS-747, which have been used clinically as antithrombotic agents. It could be shown that these drugs, via their reactive metabolites, irreversibly block the ADP receptor subtype $P2Y_{12}$.

Some $P2Y_{12}$ antagonists like AR-C69931MX (Cangrelor) or AZD6140 have reached phase III clinical studies. These inhibitors are selective platelet ADP receptor antagonists, which inhibit ADP-dependent platelet aggregation, and are effective in vivo.

Piperazino-carbonylmethylaminocarbonyl-naphtyl or -quinolyl derivatives have been described as ADP receptor antagonists in WO 02/098856 and WO 2004/052366.

WO 2006/114774 describes 2-phenyl-4-(carbonylmethylaminocarbonyl)-pyrimidine derivatives as $P2Y_{12}$ receptor antagonists.

DESCRIPTION OF THE INVENTION

The inventors have now found that the 2-phenyl-4-cyclopropyl-pyrimidine derivatives according to the present invention surprisingly show significantly improved biological properties compared to the corresponding derivatives previously known to one skilled in the art which all have an ethoxycarbonyl substitution on one of the nitrogen atoms of the piperazine group of the molecule.

Various embodiments of the invention are presented hereafter:

i) The present invention firstly relates to the compounds of formula I

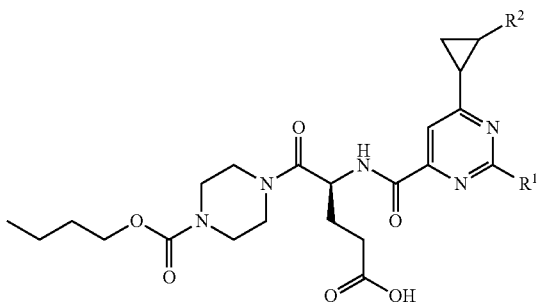

wherein $R^1$ represents phenyl optionally substituted once by halogen, methyl, methoxy, trifluoromethyl or trifluoromethoxy; and $R^2$ represents hydrogen, hydroxymethyl or alkoxymethyl; and to the salts (in particular pharmaceutically acceptable salts) of such compounds.

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art.

The compounds of formula I are $P2Y_{12}$ receptor antagonists. Accordingly, they are useful in therapy (including combination therapy), where they can be widely used as inhibitors of platelet activation, aggregation and degranulation, as promoters of platelet disaggregation or as anti-thrombotic agents.

The following paragraphs provide definitions of the various chemical moieties for the compounds according to the invention. Said definitions are intended to apply uniformly throughout the specification and claims unless an otherwise expressly set out definition provides a broader or narrower definition.

The term "halogen" refers to fluorine, chlorine, bromine or iodine, preferably to fluorine, chlorine or bromine and more preferably to fluorine.

The term "alkyl", used alone or in combination, refers to a saturated straight or branched chain alkyl group containing 1 to 7 carbon atoms (e.g. methyl, ethyl, n-propyl, iso-propyl, n-butyl, iso-butyl, sec-butyl, tert-butyl, n-pentyl, neopentyl, iso-pentyl, n-hexyl, iso-hexyl, n-heptyl or iso-heptyl), and preferably 1 to 4 carbon atoms. Representative examples of preferred alkyl groups include methyl, ethyl, propyl, iso-propyl, n-butyl, iso-butyl, sec-butyl and tert-butyl.

The term "alkoxy", used alone or in combination, refers to a saturated straight or branched chain alkoxy group containing 1 to 6 carbon atoms (e.g. methoxy, ethoxy, n-propoxy, iso-propoxy, n-butoxy, iso-butoxy, sec-butoxy, tert-butoxy, n-pentoxy, neopentyloxy, iso-pentyloxy, n-hexyloxy or iso-hexyloxy), and preferably 1 to 4 carbon atoms. Representative examples of preferred alkoxy groups include methoxy, ethoxy, propoxy, iso-propoxy, n-butoxy, iso-butoxy, sec-butoxy and tert-butoxy.

The term "alkoxymethyl", as used herein, refers to a methyl group wherein one hydrogen atom has been replaced by an alkoxy group as previously defined. Examples of alkoxymethyl groups include, but are not limited to, methoxymethyl and ethoxymethyl.

Besides, the following paragraphs provide definitions of various other terms. Said definitions are intended to apply uniformly throughout the specification and claims unless an otherwise expressly set out definition provides a broader or narrower definition.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively the term "around") placed before a temperature "Y" refers in the current application to an interval extending from the temperature Y minus 10° C. to Y plus 10° C., and preferably to an interval extending from Y minus 5° C. to Y plus 5° C.

ii) In particular, the invention relates to compounds of formula I that are also compounds of formula $I_{CE}$

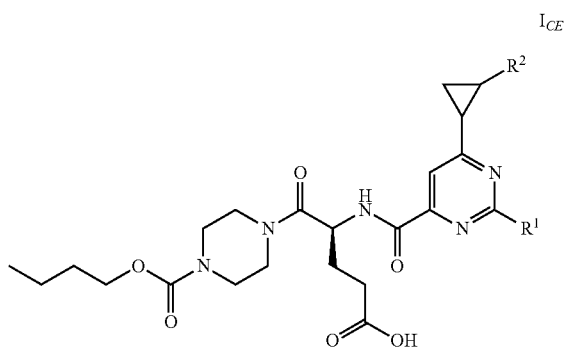

$I_{CE}$ wherein
$R^1$ represents phenyl optionally substituted once by halogen (especially fluorine); and $R^2$ represents hydrogen, hydroxymethyl or alkoxymethyl;
and to salts (in particular pharmaceutically acceptable salts) of compounds of formula $I_{CE}$.

iii) According to one preferred embodiment of this invention, the compounds of formula I as defined in embodiment i) above or their salts (among which the pharmaceutically acceptable salts will be preferred) will be such that $R^1$ represents phenyl optionally substituted once by halogen, methyl or trifluoromethyl.

iv) Preferably, the compounds of formula I as defined in embodiment i) or ii) above or their salts (among which the pharmaceutically acceptable salts will be preferred) will be such that $R^1$ represents phenyl optionally substituted once by halogen.

v) More preferably, the compounds of formula I as defined in embodiment i) or ii) above or their salts (among which the pharmaceutically acceptable salts will be preferred) will be such that $R^1$ represents phenyl optionally substituted once by fluorine (especially such that $R^1$ represents phenyl or 4-fluorophenyl, and notably such that $R^1$ represents phenyl).

vi) According to one particular embodiment of this invention, the compounds of formula I as defined in one of embodiments i) to v) above or their salts (among which the pharmaceutically acceptable salts will be preferred) will be such that $R^2$ represents hydrogen.

vii) According to another particular embodiment of this invention, the compounds of formula I as defined in one of embodiments i) to v) above or their salts (among which the pharmaceutically acceptable salts will be preferred) will be such that $R^2$ represents hydroxymethyl or alkoxymethyl.

viii) According to one variant of embodiment vii), the compounds of formula I as defined in embodiment vii) above or their salts (among which the pharmaceutically acceptable salts will be preferred) will be such that $R^2$ represents hydroxymethyl.

ix) According to the other variant of embodiment vii), the compounds of formula I as defined in embodiment vii) above or their salts (among which the pharmaceutically acceptable salts will be preferred) will be such that $R^2$ represents alkoxymethyl (in particular methoxymethyl).

x) The following compounds of formula I as defined in embodiment i) or ii) are particularly preferred:
4-{(S)-4-carboxy-2-[(6-cyclopropyl-2-phenyl-pyrimidine-4-carbonyl)-amino]-butyryl}-piperazine-1-carboxylic acid butyl ester;
4-((S)-4-carboxy-2-{[6-(trans-2-methoxymethyl-cyclopropyl)-2-phenyl-pyrimidine-4-carbonyl]-amino}-butyryl)-piperazine-1-carboxylic acid butyl ester;
4-((S)-4-carboxy-2-{[6-((1S,2S)-2-methoxymethyl-cyclopropyl)-2-phenyl-pyrimidine-4-carbonyl]-amino}-butyryl)-piperazine-1-carboxylic acid butyl ester;
4-((S)-4-carboxy-2-{[6-((1S,2S)-2-hydroxymethyl-cyclopropyl)-2-phenyl-pyrimidine-4-carbonyl]-amino}-butyryl)-piperazine-1-carboxylic acid butyl ester;
4-((S)-4-carboxy-2-{[2-(4-fluoro-phenyl)-6-((1S,2S)-2-methoxymethyl-cyclopropyl)-pyrimidine-4-carbonyl]-amino}-butyryl)-piperazine-1-carboxylic acid butyl ester;
4-((S)-4-carboxy-2-{[6-(cis-2-methoxymethyl-cyclopropyl)-2-phenyl-pyrimidine-4-carbonyl]-amino}-butyryl)-piperazine-1-carboxylic acid butyl ester;
as well as the salts (in particular pharmaceutically acceptable salts) thereof.

xi) A further object of the invention is the compounds of formula I (or of formula $I_{CE}$), as defined in one of embodiments i) to x) above, or their pharmaceutically acceptable salts, as medicaments.

The compounds of formula I and their pharmaceutically acceptable salts can be used as medicaments, e.g. in the form of pharmaceutical compositions for enteral or parenteral administration.

xii) The invention thus also relates to pharmaceutical compositions containing at least one compound according to one of embodiments i) to x) above, or a pharmaceutically acceptable salt thereof, and a pharmaceutically acceptable carrier, diluent or excipient. In particular, the invention relates to pharmaceutical compositions containing at least one compound of formula I (or of formula $I_{CE}$) and one or more pharmaceutically acceptable carriers, diluents or excipients.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

xiii) The compounds according to formula I as defined in embodiments i) to x) above and the pharmaceutically acceptable salts thereof may be used for the preparation of a medicament, and are suitable:

for the treatment or prophylaxis of diseases including stable angina, unstable angina, myocardial infarction, embolism (including complications of atherosclerosis, notably embolic stroke), arterial thrombosis (including primary arterial thrombotic complications of atherosclerosis, notably thrombotic stroke), venous thrombosis (notably deep vein thrombosis), thrombosis secondary to vascular damage or to inflammation (including vasculitis, arteritis and glomerulonephritis), venoocclusive diseases, transient ischaemic attacks, peripheral vascular diseases, myocardial infarction with or without thrombolysis, myeloproliferative disease, thrombocythaemia, sickle cell disease, inflammatory bowel disease, thrombotic thrombocytopaenic purpura, haemolytic uraemic syndrome;

for preventing thrombotic complications of septicaemia, adult respiratory distress syndrome, anti-phospholipid syndrome, heparin-induced thrombocytopaenia and pre-eclampsia/eclampsia;

for preventing cardiovascular complications after certain surgery procedures (notably coronary revascularisation like angioplasty (PTCA), other vascular graft surgery, endarterectomy or stent placement) or after accidental trauma;

for preventing organ graft rejection.

xiv) In another embodiment, the compounds of formula I as defined in embodiments i) to x) above and the pharmaceutically acceptable salts thereof may be used for the preparation of a medicament, and are suitable for preventing complications in conditions in which vasospasms lead to vasoconstriction and thus tissue-ischemia or tissue-death (necrosis).

xv) Therefore, a particular object of this invention is the use of a compound of formula I (or of formula $I_{CE}$) as defined in one of embodiments i) to x) above, or of a pharmaceutically acceptable salt thereof, for the manufacture of a medicament for the uses listed in embodiments xiii) and/or xiv) (and in particular in embodiment xiii)) above, and for the manufacture of a medicament for the treatment of occlusive vascular disorders in general.

xvi) More generally, the invention relates to the use of a compound of formula I (or of formula $I_{CE}$) as defined in one of embodiments i) to x) above, or of a pharmaceutically acceptable salt thereof, for the manufacture of a medicament for the treatment and/or prevention of occlusive vascular disorders as well as to the use of a compound of formula I (or of formula $I_{CE}$) for the manufacture of a medicament for the treatment and/or prevention of peripheral vascular, of visceral-, hepatic- and renal-vascular, of cardiovascular and of cerebrovascular diseases or conditions associated with platelet aggregation, including thrombosis in humans and other mammals.

xvii) Among the above-mentioned uses of compounds of formula I (or of formula $I_{CE}$) or of pharmaceutically acceptable salts thereof for the manufacture of medicaments according to embodiment xv) above, the uses for manufacturing medicaments for the treatment or prophylaxis of myocardial infarction, arterial thrombosis (notably thrombotic stroke), transient ischaemic attacks, peripheral vascular disease and stable and unstable angina will be preferred.

xviii) The invention further relates to the use of a compound of formula I (or of formula $I_{CE}$) according to one of embodiments i) to x) above, or of a pharmaceutically acceptable salt thereof, for the preservation of blood products in vitro (e.g. the preservation of platelet concentrates), or for the prevention of occlusion in extra-corporeal blood or blood product treatment machines (such as renal dialysis machines or plasmapheresis machines).

xix) The invention also relates to methods of treatment for the disorders mentioned in embodiments xiii) and/or xiv) (and in particular in embodiment xiii)) above, said methods comprising the administration to a patient in need thereof of an effective amount of a compound of formula I (or of formula $I_{CE}$) according to one of embodiments i) to x), or of a pharmaceutically acceptable salt of such a compound.

Any reference to a compound of formula I or $I_{CE}$ in this text is to be understood as referring also to the salts (and especially the pharmaceutically acceptable salts) of such compounds, as appropriate and expedient. The preferences indicated for the compounds of formula I of course apply mutatis mutandis to the compounds of formula $I_{CE}$, as well as to the salts and pharmaceutically acceptable salts of the compounds of formula I or of formula $I_{CE}$. The same applies to these compounds as medicaments, to pharmaceutical compositions containing these compounds as active principles, to the uses of these compounds for the manufacture of a medicament for the treatment of the diseases according to this invention or to the compounds for the treatment of the diseases according to this invention.

According to the invention, the compounds of formula I (or of formula $I_{CE}$) can be prepared by the process described below.

Preparation of the Compounds of Formula I

Abbreviations:

The following abbreviations are used throughout the specification and the examples:

Ac acetyl
ADP adenosine diphosphate
AIBN 2,2'-azobis(2-methylpropionitrile)
aq. aqueous
BSA bovine serum albumin
CC column chromatography
DCM dichloromethane
de diastereomeric excess DIPEA diisopropylethylamine
DME 1,2-dimethoxyethane
DMF N,N-dimethylformamide
dpm decays per minute
EA ethyl acetate
EDCI N-(3-dimethylaminopropyl)-N'-ethylcarbodiimide
EDTA ethylenediaminetetraacetic acid
Et ethyl
Hept heptane
HOBT 1-hydroxybenzotriazole
HPLC High-performance liquid chromatography
HV high vacuum
LC-MS Liquid Chromatography—Mass Spectrometry
Me methyl
MTBE 2-methoxy-2-methylpropane
n-BuLi n-butyl lithium
org. organic
Pd/C palladium on carbon
Ph phenyl
PyBOP benzotriazole-1-yl-oxy-tris-pyrrolidino-phosphonium hexafluorophosphate
Rf retention factor
RT room temperature
SDS sodium dodecyl sulfate
tBu tent-butyl
TCCA trichloroisocyanuric acid
TEMPO 2,2,6,6-tetramethylpiperidine 1-oxyl radical
TFA trifluoroacetic acid
THF tetrahydrofuran
TLC thin layer chromatography
$t_R$ retention time
Tris tris(hydroxymethyl)aminomethane
Z benzyloxycarbonyl General Preparation Route:

The various compounds of formula I can be prepared using the general route summarized in Scheme 1 hereafter.

Scheme 1

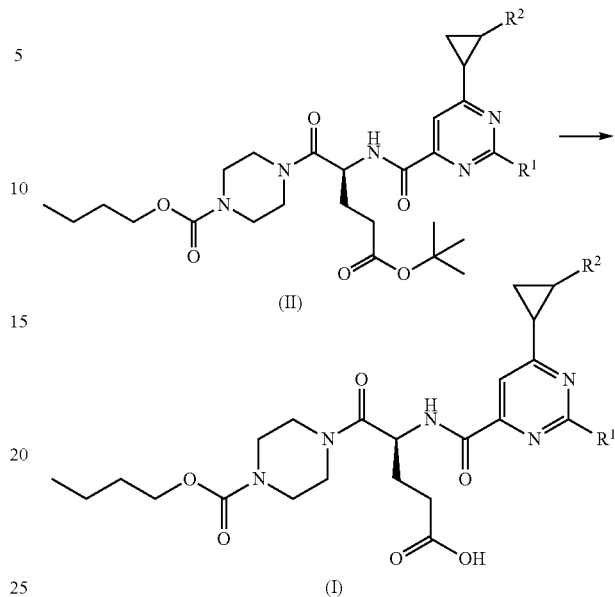

The compounds of formula I can be prepared (Scheme 1) by hydrolysis of the corresponding compounds of formula II under standard conditions well known to one skilled in the art, preferably using TFA.

Besides, whenever the compounds of formula I are obtained in the form of mixtures of diasteromers they may be separated by an appropriate combination of silica gel chromatography, HPLC and crystallisation techniques.

Preparation of the Various Synthesis Intermediates:
Preparation of the Compounds of Formula II The compounds of formula II can be prepared using the routes summarized in Scheme 2 hereafter.

Scheme 2

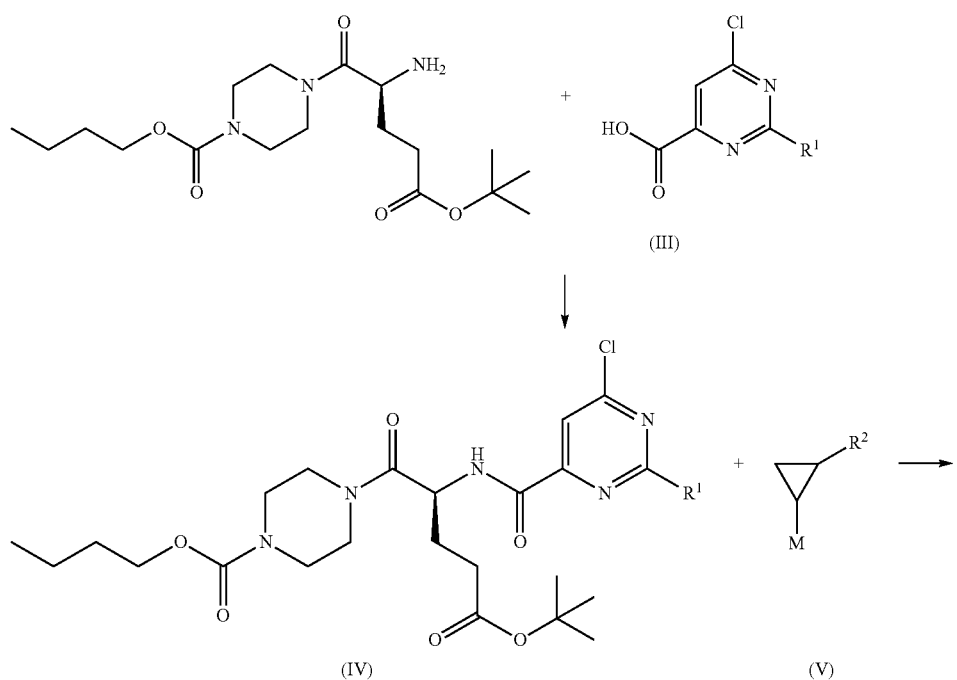

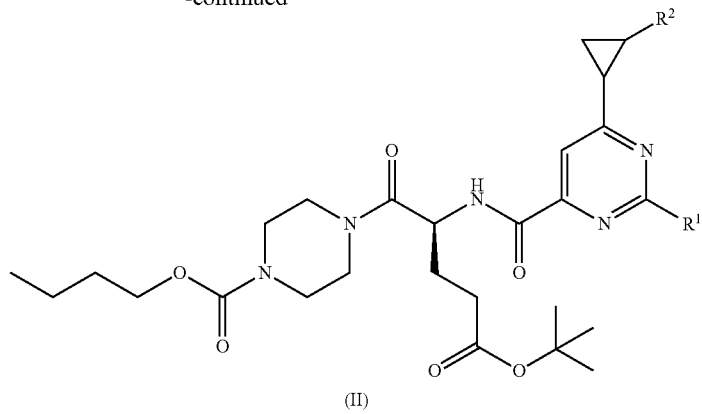

(II)

Thus, the intermediates of formula III can be coupled to 4-((S)-2-amino-4-tert-butoxycarbonyl-butyryl)-piperazine-1-carboxylic acid butyl ester, leading to the compounds of formula IV. This can be achieved using standard peptide coupling methods, using standard coupling agents such as HOBT, EDCI hydrochloride, 1,3-dicyclohexylcarbodiimide, PyBOP, benzotriazole-1-yl-oxy-tris-(dimethylamino)-phosphoniumhexafluorophosphate, optionally in the presence of a suitable base such as $NEt_3$, DIPEA or N-methylmorpholine and in a suitable solvent such as DCM, THF or DMF, preferably at a temperature around RT, or using oxalyl chloride or thionyl chloride in a suitable solvent such as DCM or MeCN, at a temperature between RT and 80° C.

The compounds of formula II can then be obtained by reacting the intermediates of formula IV with reagents of formula V wherein M is —$SnR_3$, R being alkyl, using standard conditions for a Stille reaction, and preferably a tributylstannane derivative in a suitable solvent such as toluene, and preferably heating between 110° C. and 130° C.

Alternatively, the compounds of formula II can be obtained by reacting the intermediates of formula IV with a reagent of formula V wherein M is —$B(OR')_2$, R' being hydrogen or alkyl, using standard conditions for a Suzuki reaction, and preferably a boronic acid or ester derivative in the presence of a suitable base such as $K_3PO_4$, $Na_2CO_3$ or $K_2CO_3$, in the presence of a suitable palladium catalyst such as tetrakis(triphenylphosphine)palladium in a suitable solvent such as DME/water or dioxane, and preferably heating between 80° C. and 110° C.

Preparation of the Compounds of Formula III

The compounds of formula III can be prepared as shown in Scheme 3 hereafter.

Scheme 3

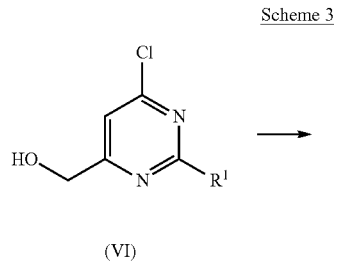

(VI)

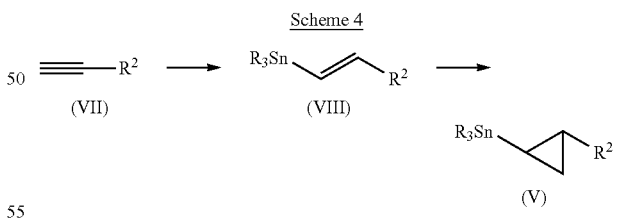

(III)

The compounds of formula III can be prepared by oxidizing the compounds of formula VI (for their preparation, see WO 2006/114774, Preparation of the compounds of formula IV, Scheme 4a), using standard oxidizing agents such as potassium permanganate, TCCA/TEMPO, in a suitable solvent such as dioxane/water, acetone/aq. $NaHCO_3$ solution, and at a temperature between 5° C. and RT.

Preparation of the Compounds of Formula V

If not commercially available, the compounds of formula V can be prepared following procedures known to one skilled in the art. In particular, the compounds of formula V wherein M is —$SnR_3$ (R being alkyl), $R^2$ is —$CH_2$—OR' (R' being hydrogen or alkyl) and the groups —$SnR_3$ and $R^2$ are in a trans arrangement can be prepared as described in Scheme 4 hereafter.

Scheme 4

$\equiv$—$R^2$ → $R_3Sn$—⧹═⧸—$R^2$ →

(VII)　　　　　(VIII)

$R_3Sn$—▷—$R^2$ (V)

The compound of formula VII wherein $R^2$ is —$CH_2$—OH can be converted (Scheme 4) into the corresponding stannanes of formula VIII wherein $R^2$ is —$CH_2$—OH through a hydrostannylation reaction according to a procedure described by Belanger G. et al. in *J. Org. Chem.* (2000), 7070-7074. Said compounds of formula VIII can then be converted into the compounds of formula V wherein $R^2$ is —$CH_2$—OH through a cyclopropanation reaction according to a procedure described by Charette A. B. et al. in *J. Am. Chem. Soc.* (1998), 120, 11943-11952. As described in this article, the cyclopropanation reaction is stereoselective if conducted in presence of a dioxaborolane ligand, leading to the compounds of formula V wherein $R^2$ is —$CH_2$—OH as single enantiomers.

Alternatively, the compounds of formula V wherein M is —$SnR_3$ (R being alkyl), $R^2$ is —$CH_2$—OR" (R" being hydrogen or alkyl) and the groups —$SnR_3$ and $R^2$ are in a cis arrangement can be prepared as described in Scheme 5 hereafter.

Scheme 5

$$\equiv\!\!-\!R^2 \longrightarrow R_3Sn\diagdown\!\!\diagup\!\!R^2 \longrightarrow$$
(VII)       (IX)

$$R_3Sn\diagdown\!\!\triangle\!\!R^2$$
(V)

The compound of formula VII wherein $R^2$ is —$CH_2$—OH can be converted into the corresponding stannanes of formula IX wherein $R^2$ is —$CH_2$—OH through a hydrostannylation reaction according to a procedure described by Sheppard G. S. et al. in *J. Med. Chem.* (2006), 3832-3849. The following step leading to the compound of formula V can be performed using the methods already described for the conversion of the compounds of formula VIII into the compounds of formula V (see Scheme 4). Finally, the compounds of formula V wherein $R^2$ is —$CH_2$—OH can then be alkylated into compounds of formula V wherein $R^2$ is —$CH_2$—OR', R' being alkyl, using standard conditions for the alkylation of a hydroxy group, using an alkylating agent of formula R'—X, X being a leaving group such as halogen, in the presence of a suitable base such as NaH, the reaction being carried out in a suitable solvent such as THF, MeCN or DMF and preferably around RT.

Preparation of 4-((S)-2-amino-4-tert-butoxycarbonyl-butyryl)-piperazine-1-carboxylic acid butyl ester The synthesis of this compound is described in the Examples (Example 1, step 1.4).

Particular embodiments of the invention are described in the following Examples, which serve to illustrate the invention in more detail without limiting its scope in any way.

EXAMPLES

Characterization Methods Used:

$^1$H-NMR (400 MHz) was carried out on a Bruker Avance 400 device. Chemical shifts are given in ppm relative to the solvent used; multiplicities: s=singlet, d=doublet, t=triplet, q=quadruplet, p=pentuplet, hex=hexet, hept=heptet, m=multiplet, br.=broad.

The LC-MS retention times have been obtained using the following elution conditions:

A Zorbax® column (Zorbax SB.AQ 5 μm, 4.6×50 mm) was used. The two elution solvents were as follows: solvent A=water+0.04% TFA; solvent B=MeCN. The eluent flow rate was 4.5 ml/min and the characteristics of the eluting mixture proportion in function of the time t from start of the elution are summarized in the table below (a linear gradient being used between two consecutive time points):

| | t (min) | | | |
|---|---|---|---|---|
| | 0 | 1 | 1.45 | 1.55 |
| Solvent A (%) | 95 | 5 | 5 | 95 |
| Solvent B (%) | 5 | 95 | 95 | 5 |

The chiral HPLC retention times for the determination of a diastereomeric excess have been obtained using the following elution conditions:

A Chiralcel column (AD-H 250×4.6 mm ID, 5 μm) was used under isocratic conditions at 25° C. The two elution solvents were as follows: solvent A=70% hexane; solvent B=EtOH 30%, 0.1% TFA. The eluent flow rate was 0.8 ml/min and the detection wavelength 210 nM.

Preparative LC-MS Methods Used:

I) Preparative LC-MS (I):

A Phenomenex® column (Gemini 10u C18 110A Ax 50×21.2 mm) was used. The two elution solvents were as follows: solvent A=water+1% formic acid; solvent B=MeCN+1% formic acid. The eluent flow rate was 50 mL/min. The characteristics of the eluting mixture proportion in function of the time t from start of the elution are summarized in the tables below (a linear gradient being used between two consecutive time points):

I) Preparative LC-MS (I):

| t (min) | 0 | 0.4 | 2.6 | 3 | 3.4 | 3.8 | 3.9 | 5 |
|---|---|---|---|---|---|---|---|---|
| Solvent A (%) | 55 | 55 | 35 | 35 | 4.5 | 4.5 | 55 | 55 |
| Solvent B (%) | 45 | 45 | 65 | 65 | 95.5 | 95.5 | 45 | 45 |

II) Preparative LC-MS (II):

A X-Terra® column (Prep MS C18 OBD™ 10u 30×75 mm) was used. The two elution solvents were as described for the preparative LC-MS (I). The eluent flow rate was 100 mL/min. The characteristics of the eluting mixture proportion in function of the time t from start of the elution are summarized in the table below (a linear gradient being used between two consecutive time points):

| t (min) | 0 | 0.6 | 3.3 | 3.9 | 4.5 | 5.1 | 6 |
|---|---|---|---|---|---|---|---|
| Solvent A (%) | 40 | 40 | 21 | 21 | 0 | 0 | 40 |
| Solvent B (%) | 60 | 60 | 79 | 79 | 100 | 100 | 60 |

Stationary Phase Used for CC:

The purifications by CC have been performed using silica gel unless otherwise specified.

Example 1

4-{(S)-4-carboxy-2-[(6-cyclopropyl-2-phenyl-pyrimidine-4-carbonyl)-amino]-butyryl}-piperazine-1-carboxylic acid butyl ester 1.1. Piperazine-1,4-dicarboxylic acid butyl ester tert-butyl ester To a solution of piperazine-1-carboxylic acid tert-butyl ester (150 g) in DCM (1.05 L) cooled at 4° C. was added $NEt_3$ (123.6 ml) followed by n-butyl chloroformate (107 mL) dropwise over 30 min. The cooling bath was removed and the reaction mixture was allowed to warm to RT over 2.5 h. Water was added, the phases were separated and the aq. phase was extracted with DCM. The combined org. phases were dried (Na$_2$SO$_4$) and evaporated off to give an oil (242.8 g). The compound was engaged directly in the next step.

TLC: (EA/Hept 1/1) Rf=0.7.

1.2. Piperazine-1-carboxylic acid butyl ester hydrochloride salt

To a cooled (15° C.) solution of intermediate 1.1 (230.5 g) in MeOH (1 L) was added 4M HCl in dioxane (604 mL). The mixture was stirred overnight at RT and evaporated to dryness. The residue was suspended in MTBE (800 mL) and the mixture was stirred for 30 min and filtered off. The solid was dried under HV to afford a white solid (176 g).

$^1$H NMR (CDCl$_3$): 10.05 (br. s, 2H), 4.21 (t, J=6.5 Hz, 2H), 3.85 (t, J=4.8 Hz, 4H), 3.22 (s, 4H), 1.69 (m, 2H), 1.39 (m, 2H), 0.96 (t, J=7.5 Hz, 3H).

1.3. 4-((S)-2-benzyloxycarbonylamino-4-tert-butoxycarbonyl-butyryl)-piperazine-1-carboxylic acid butyl ester To a solution of Z-(L)Glu(OtBu)-OH (25.2 g) in DCM/THF (240 mL/60 mL) were added EDCI hydrochloride (17.2 g), HOBT hydrate (13.7 g) and DIPEA (28.2 mL). After stirring at RT for 5 min, intermediate 1.2 (20 g) was added. The mixture was stirred at RT overnight. DCM and water were added and the phases were separated. The org. phase was washed with 2M Na$_2$CO$_3$, with 1M NaHSO$_4$ and with brine, was dried (Na$_2$SO$_4$) and evaporated off. Drying under HV gave the desired compound as an orange oil (40 g).

LC-MS: t$_R$=1.04 min; [M+H]$^+$: 506.49.

1.4. 4-((S)-2-amino-4-tert-butoxycarbonyl-butyryl)-piperazine-1-carboxylic acid butyl ester Intermediate 1.3 (40 g) was hydrogenated in MeOH (300 ml) with Pd/C (wet, 5%, 194 mg) for 24 h. The mixture was filtered through celite and evaporated off. HV drying afforded the desired compound as a light brown oil (28 g).

LC-MS: t$_R$=0.79 min; [M+H]$^+$: 372.58.

1.5. 6-chloro-2-phenyl-pyrimidine-4-carboxylic acid

To a solution of (6-chloro-2-phenyl-pyrimidin-4-yl)-methanol (240 g; prepared using a method analogous to the one described in WO 2006/114774, Example 24, intermediate 24.2) in acetone (2 L) was added an aq. NaHCO$_3$ solution (15%, 961 mL). The mixture was cooled down to 5° C. and NaBr (11.2 g) followed by TEMPO (8.56 g) were added. TCCA (506 g) was then added portionwise over 1.5 h. The resulting mixture was stirred at RT for 1.5 h. The mixture was filtered through a pad of Celite and the solution was evaporated off. The residue was diluted in water/EA. The aq. phase was extracted with EA and the combined org. phases were dried (Na$_2$SO$_4$) and evaporated off. Recrystallization of the residue (EA/Hept) afforded the desired product as a beige solid (162.1 g).

LC-MS: t$_R$=0.94 min; [M+H]$^+$: 235.18.

1.6. 4-{(S)-4-tert-butoxycarbonyl-2-[(6-chloro-2-phenyl-pyrimidine-4-carbonyl)-amino]-butyryl}-piperazine-1-carboxylic acid butyl ester To a suspension of intermediate 1.5 (17.5 g) in MeCN (600 mL) was added oxalyl chloride (12.6 mL). The mixture was heated at reflux for 2 h, cooled down to 0° C. and NEt$_3$ (31 mL) was added slowly, followed by intermediate 1.4 (27.6 g). The mixture was allowed to warm to RT, was stirred at RT for 1 h and was evaporated off. The residue was purified by CC (Hept/EA 1/0 to 1/1) afforded the desired product as a beige solid (18 g).

LC-MS: t$_R$=1.18 min; [M+H]$^+$: 588.79.

1.7. 4-{(S)-4-tert-butoxycarbonyl-2-[(6-cyclopropyl-2-phenyl-pyrimidine-4-carbonyl)-amino]-butyryl}-carboxylic acid butyl ester A mixture of intermediate 1.6 (80 mg), cyclopropylboronic acid (17 mg), K$_3$PO$_4$ (58 mg) and Pd(PPh$_3$)$_4$ (7.9 mg) in dioxane (0.5 mL) was stirred at 110° C. under argon overnight. The solvent was evaporated off. The crude was purified by preparative TLC (EA) to afford the desired compound as a yellow oil (25 mg).

LC-MS: t$_R$=1.20 min; [M+H]$^+$: 594.44.

1.8. 4-{(S)-4-carboxy-2-[(6-cyclopropyl-2-phenyl-pyrimidine-4-carbonyl)-amino]-butyryl}-piperazine-1-carboxylic acid butyl ester Intermediate 1.7 (20 mg) was dissolved in TFA (0.5 mL) and DCM (1 mL) and the mixture was stirred at RT for 4 h. The solvents were removed and the residue was purified by preparative LC-MS (I) to afford the desired compound as a white powder (3 mg).

LC-MS: t$_R$=1.06 min; [M+H]$^+$: 538.58.

Example 2

4-((S)-4-carboxy-2-{[6-(trans-2-methoxymethyl-cyclopropyl)-2-phenyl-pyrimidine-4-carbonyl]-amino}-butyryl)-piperazine-1-carboxylic acid butyl ester

2.1. (E)-3-tributylstannanyl-prop-2-en-1-ol

To neat propargyl alcohol (5 ml) were added tributyltin hydride (29.2 ml) followed by AIBN (716 mg). The mixture was heated for 2.75 h at 80° C., cooled to RT and directly purified by CC (EA/Hept 5/95) to afford the desired compound (12.9 g).

$^1$H-NMR (CDCl$_3$): 6.21 (m, 2H); 4.20 (m, 2H); 1.56-1.29 (m, 18H); 0.92 (t, 9H).

2.2. (Trans-2-tributylstannanyl-cyclopropyl)-methanol

To a solution of dimethoxyethane (0.186 mL) in anhydrous DCM (10 mL) cooled at −5° C. under argon was slowly added diethylzinc (1 M in hexane, 1.9 mL), followed by diiodomethane (0.309 mL) over a 20 min period while keeping the internal temperature around −7° C. After completion of the addition, the resulting solution was stirred for 10 min at −5° C. A solution of intermediate 2.1 (500 mg) in DCM (2 mL) was added dropwise. The cooling bath was removed, and the reaction mixture was allowed to warm to RT and was stirred overnight at RT. The reaction was quenched with an aq. NH$_4$Cl solution (1 mL), and a 1M aq. HCl solution (1 mL). The mixture was diluted with H$_2$O, the org. phase separated and the aq. phase was extracted with Et$_2$O. The combined org. phases were dried over MgSO$_4$ and evaporated off. CC (Hept/EA 95/5) gave the desired compound (374 mg).

¹H-NMR (CDCl₃): 3.58 (m, 1H); 3.42 (m, 1H); 1.57-1.47 (m, 6H); 1.38-1.28 (m, 6H); 1.10 (m, 1H); 0.92 (t, 9H); 0.83 (m, 6H); 0.78 (m, 1H); 0.55 (m, 2H); −0.30 (m, 1H).

2.3. Tributyl-(trans-2-methoxymethyl-cyclopropyl)-stannane

To a solution of intermediate 2.2 (250 mg) in THF (50 mL) was added NaH (83 mg, 60% in mineral oil) at RT, and the mixture stirred 45 min at RT. CH₃I (0.150 mL) was added and stirring was continued at RT for 15 h. The reaction mixture was diluted with water and the aq. phase was extracted several times with DCM. The combined org. phases were dried over Na₂SO₄ and evaporated off. The crude was purified by CC (Hept/EA 100/0 to 95/5) to give the desired product (248 mg).
¹H-NMR (CDCl₃): 3.45 (dd, 1H); 3.38 (s, 3H); 3.12 (dd, 1H); 1.55-1.47 (m, 6H); 1.37-1.28 (m, 6H); 1.04 (m, 1H); 0.91 (t, 9H); 0.83 (m, 6H); 0.55 (m, 2H); −0.30 (m, 1H).

2.4. 4-((S)-4-tert-butoxycarbonyl-2-{[6-(trans-2-methoxymethyl-cyclopropyl)-2-phenyl-pyrimidine-4-carbonyl]-amino}-butyryl)-piperazine-1-carboxylic acid butyl ester A solution of intermediate 2.3 (70 mg), intermediate 1.6 (100 mg) and Pd(PPh₃)₄ (11 mg) in toluene (1 mL) was degassed and heated at 130° C. overnight under argon. The mixture was evaporated off and the crude was purified by CC (Hept/EA 6/4 to 1/1) to afford the desired compound as a yellow oil (66 mg).
LC-MS: $t_R$=1.18 min; [M+H]⁺: 638.29.

2.5. 4-((S)-4-carboxy-2-{[6-(trans-2-methoxymethyl-cyclopropyl)-2-phenyl-pyrimidine-4-carbonyl]-amino}-butyryl)-piperazine-1-carboxylic acid butyl ester This compound was prepared using a method analogous to that of Example 1, step 1.8, intermediate 2.4 replacing intermediate 1.7. The compound was however purified by CC (Hept/EA 1/1), followed by preparative LC-MS (I).
LC-MS: $t_R$=1.01 min; [M+H]⁺: 582.33.

Example 3

4-((S)-4-carboxy-2-{[6-((1S,2S)-2-methoxymethyl-cyclopropyl)-2-phenyl-pyrimidine-4-carbonyl]-amino}-butyryl)-piperazine-1-carboxylic acid butyl ester

3.1. ((1R,2S)-2-tributylstannanyl-cyclopropyl)-methanol

To a solution of dimethoxyethane (0.465 mL) in anhydrous DCM (17 mL) cooled at −10° C. under argon was slowly added diethylzinc (1 M in hexane, 4.88 mL), followed by diiodomethane (0.768 mL) over a 20 min period while keeping the internal temperature around −10° C. After completion of the addition, the resulting solution was stirred for 10 min at −10° C. A solution of (4R,5R)-2-butyl-N,N,N',N'-tetramethyl-1,3,2-dioxaborolane-4,5-dicarboxamide (0.72 mL) in DCM (7 mL) was added over 5 min, immediately followed by a solution of intermediate 2.1 (826 mg) in DCM (7 mL) dropwise. The cooling bath was removed, and the reaction mixture was allowed to warm to RT and was stirred overnight at RT. The reaction was quenched with an aq. NH₄Cl solution (2 mL), and a 1M aq. HCl solution (2 mL). The mixture was diluted with H₂O, the org. phase separated and the aq. phase was extracted with DCM and Et₂O. The combined org. phases were dried over MgSO₄ and evaporated off. CC (Hept/EA 95/5) gave the desired compound (660 mg).
¹H-NMR (CDCl₃): 3.55 (dd, 1H); 3.39 (dd, 1H); 1.54-1.44 (m, 6H); 1.37-1.24 (m, 6H); 1.14-1.03 (m, 1H); 0.89 (t, 9H); 0.81 (t, 6H); 0.80-0.75 (m, 1H); 0.55-0.50 (m, 2H); −0.20-−0.30 (m, 1H).
Optical rotation (589 nm, CHCl₃, 25° C., l=10 cm, 101.6 mg in 10 mL, c=1.016):
Specific optical rotation=+14.033°.

3.2. Tributyl-((1S,2R)-2-methoxymethyl-cyclopropyl)-stannane

This compound was prepared using a method analogous to that of Example 2, step 2.3, intermediate 3.1 replacing intermediate 2.2.
¹H-NMR (CDCl₃): 3.42 (dd, 1H); 3.36 (s, 3H); 3.09 (dd, 1H); 1.54-1.43 (m, 6H); 1.36-1.24 (m, 6H); 1.03 (m, 1H); 0.89 (t, 9H); 0.80 (m, 6H); 0.54 (m, 2H); −0.30 (m, 1H).

3.3. 4-((S)-4-tert-butoxycarbonyl-2-{[6-((1S,2S)-2-methoxymethyl-cyclopropyl)-2-phenyl-pyrimidine-4-carbonyl]-amino}-butyryl)-piperazine-1-carboxylic acid butyl ester This compound was prepared using a method analogous to that of Example 2, step 2.4, intermediate 3.2 replacing intermediate 2.3.
LC-MS: $t_R$=1.17 min; [M+H]⁺: 638.3.

3.4. 4-((S)-4-carboxy-2-{[6-((1S,2S)-2-methoxymethyl-cyclopropyl)-2-phenyl-pyrimidine-4-carbonyl]-amino}-butyryl)-piperazine-1-carboxylic acid butyl ester This compound was prepared using a method analogous to that of Example 1, step 1.8, intermediate 3.3 replacing intermediate 1.7. The compound was however purified by CC (EA).
LC-MS: $t_R$=1.05 min; [M+H]⁺: 582.20.
¹H-NMR (CDCl₃): 9.13 (d, 1H); 8.50 (m, 2H); 7.84 (s, 1H); 7.51 (m, 3H); 5.32 (m, 1H); 4.14 (t, 2H); 3.80-3.48 (m, 9H); 3.42 (dd, 1H); 3.40 (s, 3H); 2.60-2.48 (m, 2H); 2.24 (m, 1H); 2.12 (m, 1H); 2.06 (m, 1H); 1.97 (m, 1H); 1.68-1.58 (m, 3H); 1.46-1.36 (m, 2H); 1.18 (m, 1H); 0.96 (t, 9H).
Chiral HPLC: $t_R$=21.87 min; 93% de.

Example 4

4-((S)-4-carboxy-2-{[6-((1S,2S)-2-hydroxymethyl-cyclopropyl)-2-phenyl-pyrimidine-4-carbonyl]-amino}-butyryl)-piperazine-1-carboxylic acid butyl ester

4.1. 4-((S)-4-tert-butoxycarbonyl-2-{[6-((1S,2S)-2-hydroxymethyl-cyclopropyl)-2-phenyl-pyrimidine-4-carbonyl]-amino}-butyryl)-piperazine-1-carboxylic acid butyl ester This compound was prepared using a method analogous to that of Example 2, step 2.4, intermediate 3.1 replacing intermediate 2.3. The compound was however purified by CC (Hept/EA 1/1 to 3/7, then EA).
LC-MS: $t_R$=1.11 min; [M+H]⁺: 624.26.

4.2. 4-((S)-4-carboxy-2-{[6-((1S,2S)-2-hydroxymethyl-cyclopropyl)-2-phenyl-pyrimidine-4-carbonyl]-amino}-butyryl)-piperazine-1-carboxylic acid butyl ester This compound was prepared using a method analogous to that of Example 1, step 1.8, intermediate 4.1 replacing intermediate 1.7. The crude compound was however taken up in MeOH/NaOH (3 mL/1M, 3 mL) and the mixture was stirred at RT for 30 min. The mixture was acidified (1M HCl) and extracted with DCM. The combined org. phases were dried over MgSO$_4$ and evaporated off. The residue was purified by preparative TLC (Hept/EA/AcOH 95/5/0.1).
LC-MS: $t_R$=0.97 min; [M+H]$^+$: 568.45.

Example 5

4-((S)-4-carboxy-2-{[2-(4-fluoro-phenyl)-6-((1S,2S)-2-methoxymethyl-cyclopropyl)-pyrimidine-4-carbonyl]-amino}-butyryl)-piperazine-1-carboxylic acid butyl ester

5.1. 4-fluoro-benzamidine

To an ice-cold solution of hexamethyldisilazane (7 ml) in Et$_2$O (40 ml) was added n-BuLi (1.6M in hexanes, 20.6 ml), followed by a solution of 4-fluorobenzonitrile (2 g) in Et$_2$O (10 ml). After stirring at 0° C. for 10 min, the mixture was allowed to warm to RT and was stirred at RT for 20 h. The mixture was acidified to pH 1 by adding a 1M HCl solution and was washed with CHCl$_3$. The aqueous layer was then basified to pH 14 by adding Na$_2$CO$_3$ and NaOH and was extracted twice with CHCl$_3$. The org. layers were dried (Na$_2$SO$_4$) and evaporated off to afford the desired compound (1.59 g).
LC-MS: $t_R$=0.33 min; [M+H]$^+$: 139.21.

5.2. 6-chloro-2-(4-fluoro-phenyl)-pyrimidine-4-carboxylic acid

This compound was prepared in 4 steps from intermediate 5.1 using methods analogous to those described in WO 2006/114774, Example 1, step 1.3 and Example 24, steps 24.1, 24.2 and 24.3.
LC-MS: $t_R$=0.90 min; [M+H]$^+$: 253.24.

5.3. 4-((S)-4-tert-butoxycarbonyl-2-{[6-chloro-2-(4-fluoro-phenyl)-pyrimidine-4-carbonyl]-amino}-butyryl)-piperazine-1-carboxylic acid butyl ester This compound was prepared using a method analogous to that of Example 1, step 1.6, intermediate 5.2 replacing intermediate 1.5.
LC-MS: $t_R$=1.19 min; [M+H]$^+$: 606.09.

5.4. 4-((S)-4-tert-butoxycarbonyl-2-{[2-(4-fluoro-phenyl)-6-((1S,2S)-2-methoxymethyl-cyclopropyl)-pyrimidine-4-carbonyl]-amino}-butyryl)-piperazine-1-carboxylic acid butyl ester This compound was prepared using a method analogous to that of Example 2, step 2.4, intermediate 5.3 replacing intermediate 2.3. The compound was however purified by preparative LC-MS (II).
LC-MS: $t_R$=1.19 min; [M+H]$^+$: 656.22.

5.5. 4-((S)-4-carboxy-2-{[2-(4-fluoro-phenyl)-6-((1S,2S)-2-methoxymethyl-cyclopropyl)-pyrimidine-4-carbonyl]-amino}-butyryl)-piperazine-1-carboxylic acid butyl ester This compound was prepared using a method analogous to that of Example 1, step 1.8, intermediate 5.4 replacing intermediate 1.7. The compound was however purified by preparative TLC (DCM/acetone/AcOH 5/3/0.1).
LC-MS: $t_R$=1.06 min; [M+H]$^+$: 600.32.

Example 6

4-((S)-4-carboxy-2-{[6-(cis-2-methoxymethyl-cyclopropyl)-2-phenyl-pyrimidine-4-carbonyl]-amino}-butyryl)-piperazine-1-carboxylic acid butyl ester

6.1. (Cis-2-tributylstannanyl-cyclopropyl)-methanol

This compound was prepared using a method analogous to that of Example 2, step 2.2, (Z)-3-tributylstannanyl-prop-2-en-1-ol (Sheppard et al., *J. Med. Chem.* (2006), 49, 3832) replacing intermediate 2.1.
$^1$H-NMR (CDCl$_3$): 3.56-3.60 (m, 1H); 3.25-3.30 (m, 1H); 1.48-1.60 (m, 6H); 1.28-1.44 (m, 8H); 0.84-0.94 (m, 16H); 0.20-0.24 (m, 1H); −0.02-0.04 (m, 1H).

6.2. Tributyl-(cis-2-methoxymethyl-cyclopropyl)-stannane

This compound was prepared using a method analogous to that of Example 2, step 2.3, intermediate 6.1 replacing intermediate 2.2.
$^1$H-NMR (CDCl$_3$): 3.35 (s, 3H); 3.30-3.34 (m, 1H); 3.09-3.13 (m, 1H); 1.48-1.57 (m, 6H); 1.28-1.39 (m, 8H); 0.83-0.94 (m, 16H); 0.24-0.28 (m, 1H); −0.04-0.02 (m, 1H).

6.3. 4-((S)-4-tert-butoxycarbonyl-2-{[6-(cis-2-methoxymethyl-cyclopropyl)-2-phenyl-pyrimidine-4-carbonyl]-amino}-butyryl)-piperazine-1-carboxylic acid butyl ester This compound was prepared using a method analogous to that of Example 2, step 2.4, intermediate 6.2 replacing intermediate 2.3. The compound was however purified twice by CC (first CC: Hept/EA 1/1 to 3/7, then EA; second CC: Hept/EA 1/0 to 1/1).
LC-MS: $t_R$=1.17 min; [M+H]$^+$: 638.38.

6.4. 4-((S)-4-carboxy-2-{[6-(cis-2-methoxymethyl-cyclopropyl)-2-phenyl-pyrimidine-4-carbonyl]-amino}-butyryl)-piperazine-1-carboxylic acid butyl ester This compound was prepared using a method analogous to that of Example 1, step 1.8, intermediate 6.3 replacing intermediate 1.7.
LC-MS: $t_R$=1.03 min; [M+H]$^+$: 582.42.
Biological Tests
P2Y$_{12}$ Receptor Binding Assay
Procedure
Chinese Hamster Ovary (CHO) cells with recombinant expression of the human P2Y$_{12}$ receptor were cultured in 24 well cell-culture plates. Cells were washed three times with binding buffer (50 mM Tris pH 7.4, 100 mM NaCl, 1 mM EDTA, 0.5% BSA). The cells were then incubated with 0.5 ml per well binding buffer containing tritium-labeled 2-methylthio-adenosine 5'-diphosphate (2-methyl-S-ADP) (between 100'000 and 300'000 dpm per well) and various concentrations of test compounds. After incubation at RT for 2 hours, cells were washed three times with binding buffer. Then, cells were solubilized by addition of 0.5 ml solubilization buffer (SDS, NaOH, EDTA). The content of each well was then transferred into beta-counter vials and 2.0 ml of Ultima Gold Scintillation liquid was added. After quantification of the cell-associated signal, extent of inhibition was calculated relative to maximal possible inhibition demonstrated by addition of excess of cold 2-methyl-S-ADP.

Results

The results shown in the following tables could be obtained for the Example and reference compounds using the procedure described above for the $P2Y_{12}$ receptor binding assay:

| Example No. | $IC_{50}$ (nM) |
|---|---|
| 1 | 6 |
| 2 | 3 |
| 3 | 5 |
| 4 | 4 |
| 5 | 2 |
| 6 | 9 |

| Compound structure | $IC_{50}$ (nM) |
|---|---|
| 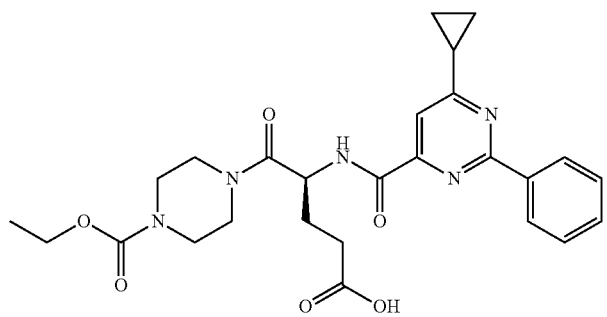 [SMILES: CCOC(=O)N1CCN(C(=O)[C@H](CCC(=O)O)NC(=O)c2cc(C3CC3)nc(-c3ccccc3)n2)CC1] [compound of Example 90 of WO 2006/114774] | 43 |
| 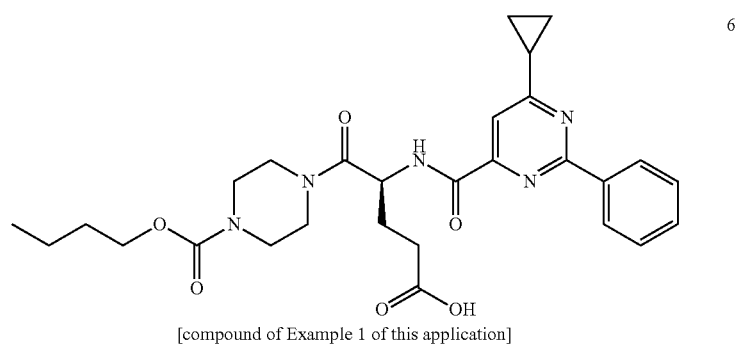 [compound of Example 1 of this application] | 6 |
| 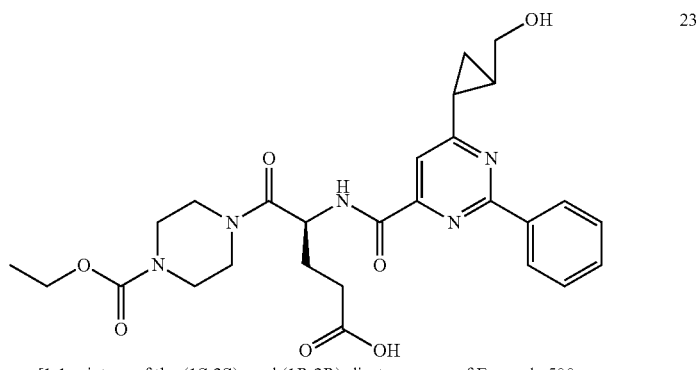 [1:1 mixture of the (1S,2S)- and (1R,2R)-diastereomers of Example 500 of WO 2006/114774] | 23 |

| Compound structure | IC$_{50}$ (nM) |
|---|---|
| 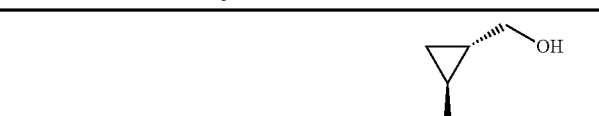 [compound of Example 4 of this application] | 4 |

The invention claimed is:

1. A compound of formula I

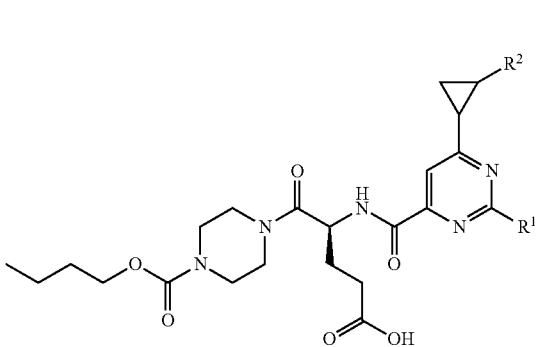

wherein
R$^1$ represents phenyl optionally substituted once by halogen, methyl, methoxy, trifluoromethyl or trifluoromethoxy; and
R$^2$ represents hydrogen, hydroxymethyl or alkoxymethyl;
or a salt of such a compound.

2. A compound according to claim 1, which is also a compound of formula I$_{CE}$

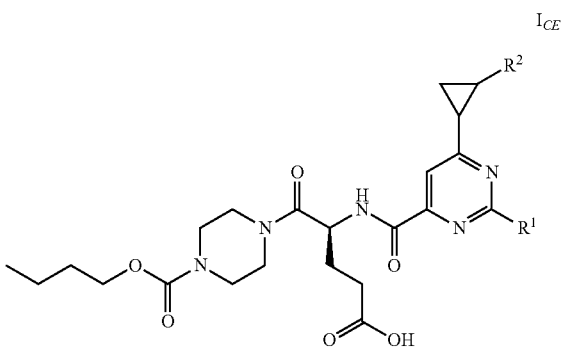

wherein
R$^1$ represents phenyl optionally substituted once by halogen; and
R$^2$ represents hydrogen, hydroxymethyl alkoxymethyl;
or a salt of such a compound.

3. A compound according to claim 1, wherein R$^1$ represents phenyl optionally substituted once by fluorine;
or a salt of such a compound.

4. A compound according to claim 1, wherein R$^2$ represents hydrogen;
or a salt of such a compound.

5. A compound according to claim 1, wherein R$^2$ represents hydroxymethyl or alkoxymethyl;
or a salt of such a compound.

6. A compound according to claim 5, wherein R$^2$ represents hydroxymethyl;
or a salt of such a compound.

7. A compound according to claim 5, wherein R$^2$ represents alkoxymethyl;
or a salt of such a compound.

8. A compound according to claim 1, which is selected from the group consisting of:
  4-{(S)-4-carboxy-2-[(6-cyclopropyl-2-phenyl-pyrimidine-4-carboyl)amino]-butyryl}-piperazine-1-carboxylic acid butyl ester;
  4-((S)-4-carboxy-{[6-(trans-2-metoxymethyl-cyclopropyl)-2-phenyl-pyrimidine-4-carbonyl]-amino}-butyryl)-piperazine-1-carboxylic acid butyl ester;
  4-((S)-4-carboxy-2-{[6-((1S,2S)-2-methoxymethyl-cyclopropyl)-phenyl-pyrimidine-4-carbonyl]-amino}-butyryl)-piperazine-1-carboxylic acid butyl ester;
  4-((S)-4-carboxy-2-{[6-((1S,2S)-2-hydroxymethyl-cyclopropyl)-2-phenyl-pyrimidine-4-carbonyl]amino}-butyryl)-piperazine-1-carboxylic acid butyl ester;
  4-((S)-4-carboxy-2-({[2-4-fluoro-phenyl)-6-((1S,2S)-methoxymethyl-cyclopropyl)-pyrimidine-4-carbonyl]amino}-butyryl)-piperazine-1-carboxylic acid butyl ester;
  4-((S)-4-carboxy-2-{[6-(cis-2-methoxymethyl-cyclopropyl)-2-phenyl-pyrimidine-4-carbonyl]-amino}-butyryl)-piperazine-1-carboxylic acid butyl ester;
  or a salt of such a compound.

9. A pharmaceutical composition containing at least one compound according to claim 1, or a pharmaceutically acceptable salt thereof, and one or more pharmaceutically acceptable carriers, diluents or excipients.

10. A method for the treatment of thrombosis comprising administering to a subject a pharmaceutically active amount of a compound according to claim 1, or of a pharmaceutically acceptable salt thereof.

* * * * *

UNITED STATES PATENT AND TRADEMARK OFFICE
CERTIFICATE OF CORRECTION

PATENT NO. : 8,466,156 B2  
APPLICATION NO. : 12/936664  
DATED : June 18, 2013  
INVENTOR(S) : Eva Caroff and Emmanuel Meyer Page 1 of 1

It is certified that error appears in the above-identified patent and that said Letters Patent is hereby corrected as shown below:

In the Specifications

Column 1, lines 9-10, "IB32009/051499, filed on Apr. 9, 2009, which claims the benefit of PCT Application No. PCT/IB2008/051385, filed on" should read:
-- IB2009/051498, filed on Apr. 9, 2009, which claims the benefit of PCT Application No. PCT/IB2008/051389, filed on --.

In the Claims

Claim 2, column 21, line 66, "$R^2$ represents hydrogen, hydroxymethyl alkoxymethyl;" should read:
-- $R^2$ represents hydrogen, hydroxymethyl or alkoxymethyl; --.

Claim 8, column 22, lines 38-40, "4-{(S)-4-carboxy-2-[(6-cyclopropyl-2-phenyl-pyrimidine-4-carboyl)amino]-butyryl}-piperazine-1-carboxylic acid butyl ester;" should read:
-- 4-{(S)-4-carboxy-2-[(6-cyclopropyl-2-phenyl-pyrimidine-4-carbonyl)-amino]-butyryl}-piperazine-1-carboxylic acid butyl ester; --.

Claim 8, column 22, lines 41-43, "4-((S)-4-carboxy-{[6-(trans-2-metoxymethyl-cyclopropyl)-2-phenyl-pyrimidine-4-carbonyl]-amino}-butyryl)-piperazine-1-carboxylic acid butyl ester;" should read:
-- 4-((S)-4-carboxy-2-{[6-(trans-2-methoxymethyl-cyclopropyl)-2-phenyl-pyrimidine-4-carbonyl]-amino}-butyryl)-piperazine-1-carboxylic acid butyl ester; --.

Claim 8, column 22, lines 44-46, "4-((S)-4-carboxy-2-{[6-((1S,2S)-2-methoxymethyl-cyclopropyl)-phenyl-pyrimidine-4-carbonyl]-amino}-butyryl)-piperazine-1-carboxylic acid butyl ester;" should read:
-- 4-(S)-4-carboxy-2-{[6-((1S,2S)-2-methoxymethyl-cyclopropyl)-2-phenyl-pyrimidine-4-carbonyl]-amino}-butyryl)-piperazine-1-carboxylic acid butyl ester; --.

Claim 8, column 22, lines 47-49, "4-((S)-4-carboxy-2-{[6-((1S,2S)-2-hydroxymethyl-cyclopropyl)-2-phenyl-pyrimidine-4-carbonyl]amino}-butyryl)-piperazine-1-carboxylic acid butyl ester;" should read:
-- 4-((S)-4-carboxy-2-{[6-((1S,2S)-2-hydroxymethyl-cyclopropyl)-2-phenyl-pyrimidine-4-carbonyl]-amino}-butyryl)-piperazine-1-carboxylic acid butyl ester; --.

Claim 8, column 22, lines 50-53, "4-((S)-4-carboxy-2-({[2-4-fluoro-phenyl)-6-((1S,2S)-methoxymethyl-cyclopropyl)-pyrimidine-4-carbonyl]amino}-butyryl)-piperazine-1-carboxlic acid butyl ester;" should read:
-- 4-((S)-4-carboxy-2-{[2-(4-fluoro-phenyl)-6-((1S,2S)-2-methoxymethyl-cyclopropyl)-pyrimidine-4-carbonyl]-amino}-butyryl)-piperazine-1-carboxylic acid butyl ester; --.

Signed and Sealed this  
First Day of October, 2013

Teresa Stanek Rea  
*Deputy Director of the United States Patent and Trademark Office*

UNITED STATES PATENT AND TRADEMARK OFFICE
CERTIFICATE OF CORRECTION

PATENT NO.       : 8,466,156 B2
APPLICATION NO. : 12/936664
DATED            : June 18, 2013
INVENTOR(S)      : Caroff et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 200 days.

Signed and Sealed this
Eighth Day of September, 2015

Michelle K. Lee
*Director of the United States Patent and Trademark Office*